United States Patent [19]

Folsom

[11] Patent Number: 4,840,169

[45] Date of Patent: Jun. 20, 1989

[54] VENTILATION SYSTEM FOR ARTISTS

[76] Inventor: Fred Folsom, 908 Hudson Ave., Takoma Park, Md. 20912

[21] Appl. No.: 136,521

[22] Filed: Dec. 22, 1987

Related U.S. Application Data

[63] Continuation of Ser. No. 929,836, Nov. 13, 1986, abandoned.

[51] Int. Cl.[4] .............................................. A61B 19/00

[52] U.S. Cl. .................................. 128/863; 98/115.3; 128/910

[58] Field of Search ................. 128/910, 205, 17, 139, 128/1 R, 132 R; 98/115.1, 115.2, 115.3; 141/93; 55/436, 437, 385 A, 385 C

[56] References Cited

U.S. PATENT DOCUMENTS

| | | | |
|---|---|---|---|
| 2,341,628 | 2/1944 | Koweindl | 55/385 A |
| 2,576,008 | 11/1951 | Gladfelter et al. | 98/115.2 |
| 3,072,040 | 1/1963 | Triplett | 98/115.3 |
| 3,727,540 | 4/1973 | Galluzzo | 98/115.3 |
| 4,014,658 | 3/1977 | Arendsen et al. | 141/93 |
| 4,071,338 | 1/1978 | Hutter, III et al. | 128/910 |
| 4,312,291 | 1/1982 | Knab | 98/115.3 |
| 4,351,863 | 9/1982 | Roesner | 98/115.2 |
| 4,647,295 | 3/1987 | Christ | 98/115.1 |

FOREIGN PATENT DOCUMENTS

| | | | |
|---|---|---|---|
| 2070940 | 9/1981 | United Kingdom | 128/910 |

*Primary Examiner*—Edward M. Coven
*Assistant Examiner*—J. P. Lacyk
*Attorney, Agent, or Firm*—Fleit, Jacobson, Cohn & Price

[57] ABSTRACT

A ventilation system for use by artists when working with paints and solvents is disclosed. The system includes a palette assembly wherein a palette is mounted on the inside of a housing which is connected to a blower so as to create a negative air pressure in the housing to force harmful vapors through the housing, into the blower, and away from the artist. The system also includes a respiration unit to be used by the artist when mixing paints and solvents or painting with them. The unit includes a compressor (air pump) which is placed in clean air and provides a supply of air, a filter for further purifying the air, and a mask for receiving the fresh air for use in a studio. In an alternate embodiment, the mask further includes rebreather bag to ensure the user of a sufficient supply of purified air at lower SCFM output.

6 Claims, 2 Drawing Sheets

VENTILATION SYSTEM FOR ARTISTS

This application is a contiuation of application Ser. No. 929,836, filed Nov. 13, 1986 now abandoned.

BACKGROUND OF THE INVENTION

The present invention relates to a system for improving ventilation when working with solvents that possess harmful vapors.

When an artist works with paints, it is often necessary to use solvents which possess harmful vapors. This is particularly the case when an artist is working with oil based paints. Specifically, vapors from the solvents can cause physiological problems when mixing the paints, or when painting with them. Turpentine, and other solvents possess vapors which are harmful to a large percentage of the population. The harmful medical effects can be caused either by allergies to the solvents, or toxic reactions. The presence of the solvent vapors can cause any of the following symptoms or complications.

1. Irritation of eyes, nose, throat, lungs or skin, including rashes and hypersensitivities
2. Headaches and dizziness
3. Deep aching in the chest
4. Trembling and nervous disorders
5. Redness of the face, ears and eyes
6. Poor concentration, and a stunned sensation while working with solvents, developing later into lethargy and sickness
7. Hyperemotional behavior, irritability and apprehensiveness
8. Low grade fever
9. Tachycardia
10. Chronic system poisoning leading to liver, kidney or heart disease.

Because of these medical symptoms and complications, it is desirable to minimize the exposure to harmful vapors when working with paint solvents. For example, when mixing paints on a palette, it would be desirable to draw the harmful fumes away from the artist. Additionally, when painting with oil based paints, it would be desirable to minimize the exposure of the artist to hazardous fumes.

Therefore, there exists a need for a system to provide an artist with adequate ventilation so that, when mixing paints on a palette, the harmful solvent vapors are drawn away from the painter, and when painting with oil based paints, the artist's exposure to harmful vapors would be minimized.

SUMMARY OF THE INVENTION

Thus, a purpose of the present invention is to provide a ventilation system wherein an artist is protected from harmful solvent vapors. Specifically, when mixing paints, the system uses a down draft palette which is designed to draw solvent vapors away from the artist. Most toxic fumes which are heavier than air are released during mixing on a palette. The down draft palette assembly is designed so that the mixing palette itself is set inside a box which is connected to a negative pressure source. The length and width of the box are both slightly larger than the length and width of the palette. To operate the palette assembly, the negative pressure source is activated to draw vapors created by the solvents and paints away from the artist and towards the source. When the artist is not using the palette, the negative pressure source is turned off, and a lid is placed onto the top of the box to enclose the mixing palette assembly. Further, when mixing paints or when painting, the system also includes a respiration system wherein uncontaminated air is supplied to an artist through a respirator mask which is to be worn while painting. The respiration system further includes a high grade filter to purify air and a rebreather bag to provide the artist with a sufficient supply of fresh uncontaminated air.

Thus, it is an object of the present invention to provide a ventilation system to protect an artist from being exposed to harmful vapors when working with oil based paints.

It is a further object of the present invention to provide a palette assembly designed to draw harmful volatile solvent vapors away from the artist.

A further object of the present invention is to provide a respiration system wherein the artist is continuously provided with fresh uncontaminated air while painting.

A further object of the present invention is to provide a palette assembly which can either be portable or mounted to an existing structure, such as a table and is connected to a blower that hooks over a window sill to exhaust harmful gases.

It is an additional object of the present invention to provide a palette assembly which is of simple construction and may be made of ordinary materials such as plastic and glass.

A further object of the present invention is to provide a respiration system which provides fresh air to the artist wherein a portable, small volume air compressor pump is to be used in combination with a rebreather oxygen mask.

Other objects and features of the present invention will become apparent to those skilled in the art as the disclosure is made in the following description of the preferred embodiment of the present invention, as illustrated in the accompanying drawings.

DETAILED DESCRIPTION OF THE DRAWINGS

Figure 1:
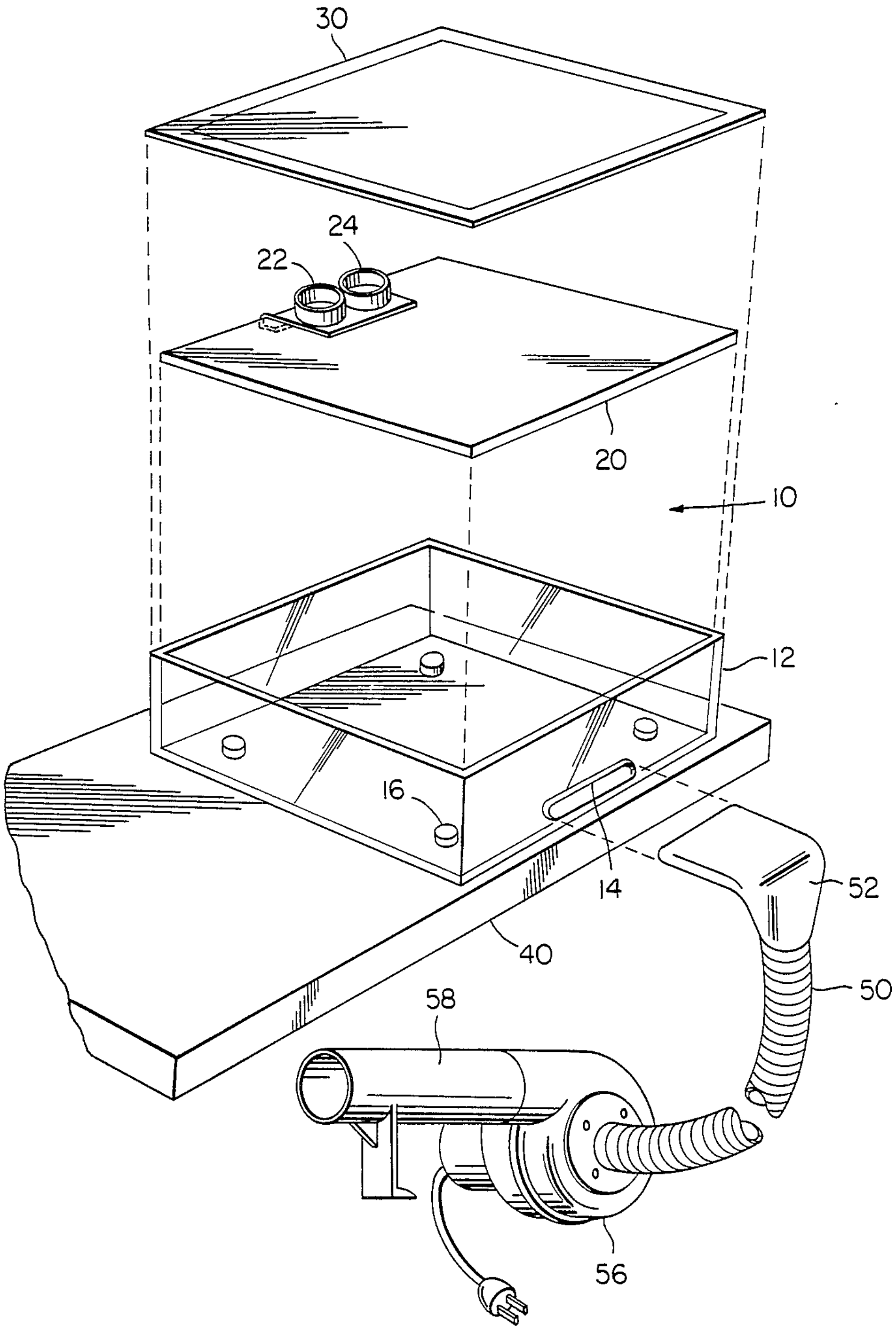
FIG. 1 is a perspective view of a down draft palette assembly embodying the teachings of the instant invention for use when mixing paints with solvents and/or painting.
Figure 2:
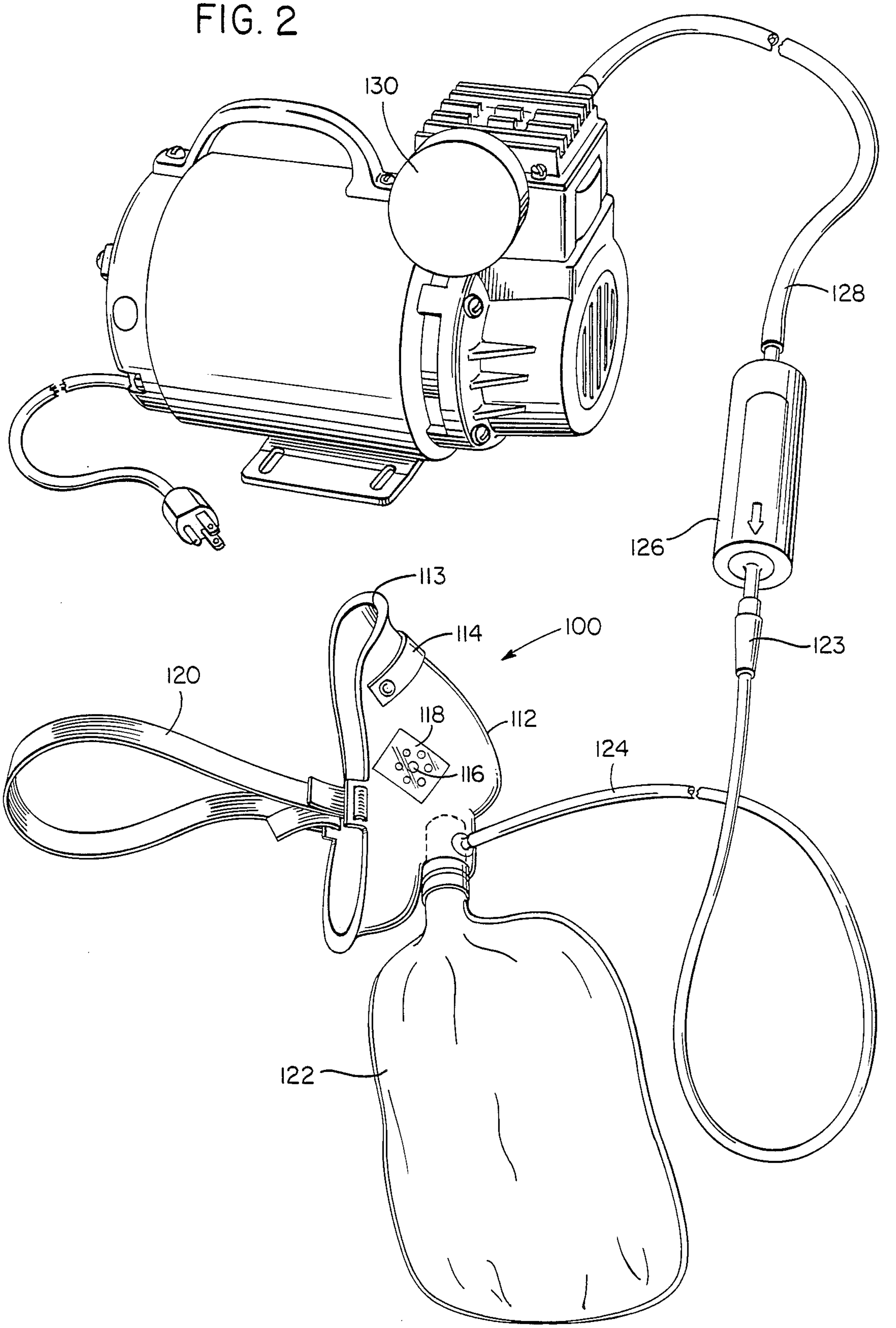
FIG. 2 is a view of a respiration system embodying the teachings of the instant invention for use when the artist is mixing paints and/or painting or varnishing.

In describing the invention illustrated in the drawings, specific terminology will be resorted to for the sake of clarity. However, the invention is not intended to be limited to the specific terms so selected, and it is to be understood that each specific term selected includes all technical equivalents which operate in a similar manner to accomplish a similar purpose.

Referring now to the drawings, and more particularly FIG. 1, the basic elements of the palette assembly for use in traditional easel painting of the present invention are collectively designated as 10. Assembly 10 includes hollow box 12, palette 20, which is mounted inside box 12, and lid 30, which is used to enclose box 12, when the palette is not in use.

Box 12 is preferably made of clear plastic, and can be of any desired size. In particular, the inventor has discovered that sizes of 10 inches by 13 inches, 13 inches by 17 inches and 19 inches by 25 inches are particularly suitable. Box 12 also has located in the lower portion of one of its sidewalls oblong hole 14. Hole 14 may be of any desired size but is preferably six inches long and ¾ inch high so that it may be connected to a 45 degree vacuum head.

Further, the inside of bottom surface of box 12 has extensions 16 designed to hold palette 20. Extensions 16 may be of any desired size, and in the preferred embodiment, are four ¾ to 1 inch risers mounted inwardly towards the center of the bottom surface of box 12.

When mixing paints, palette 20 is set on extensions 16. In the preferred embodiment of the invention, palette 20 is made of glass. Further, the palette is to be designed so that its length and width are each approximately one inch less than the respective length and width of box 12. Therefore, preferred dimensions for palette 20 are 9 inches by 12 inches, 12 inches by 16 inches, or 18 inches by 24 inches. Palette 20 has, on its upper surface, mixing cups 22 and 24 to act as storage receptacles for the solvent mediums used to mix paints.

Lid 30 is designed to enclose box 12 when palette 20 is not in use. Lid 30 may be made of any suitable material, preferably plastic, and is designed to directly rest on the upper surfaces of box 12. In alternative embodiments, lid 30 may be hingedly mounted to box 12 (not pictured), snapped onto box 12 or have provided, on its lower surface, protrusions (not pictured) which contact the inside surface of the upright walls of box 12 to further aid in securing lid 30 to box 12. Lid 30 acts as a further aid in limiting exposure to harmful fumes.

To operate assembly 10, hose 50 is connected to negative pressure blower 56 at one end and is connected to vacuum head 52 at the other end. A recommended blower which is overload protected and fire safe is a two inch shaded pole squirrel cage blower. Larger blowers may be used in connection with larger palettes. In the preferred embodiment, hose 50 is two inches in diameter and made of collapsible plastic and is located 6 inches under palette 20 and vacuum head 52 is inserted flush through exact size portion of hole 14. Securing vacuum head 52 to hole 14 is accomplished by any suitable means, such as compatlibly crafted coupling. When vacuum head 52 is secured in hole 14, it should longitudinally extend below palette 20, preferably at least one third of the way. This maximizes the exhausting of harmful solvent vapors. Negative pressure blower 56 is preferably mounted on the inside of a window sill and is additionally connected to outlet hose 58 which vents the drawn in air to the outside. Further, vacuum head 52 bends downward to allow hose 50 to drop parallel to box 12 and extends the negative pressure towards the center of the underside of palette 20.

When mixing paints or painting, palette 20 is laid onto extensions 16 so that there exists air space in lengthwise, widthwise and heightwise directions around palette 20. Blower 56 is activated so as to form a negative pressure around the outer perimeter of palette 20 and through vacuum head 52. Thereafter, solvents are placed into cups 22 and 24 so that mixing of the materials can be effectuated. A negative air pressure should have already been created in box 12 so that when pouring solvents into cups 22 and 24, the heavier than air harmful vapors are drawn through vacuum head 52 towards blower 56 and away from the artist's studio and out the window. Mixing the paints then occurs on palette 20 and continues while the artist is painting.

After mixing and painting has been completed, palette 20 remains permanently mounted inside box 12, and lid 30 is placed on the outside upper periphery of box 12 to enclose assembly 10. Blower 56 remains activated for a suitable period of time during painting and cleanup to eliminate harmful vapors. Thereafter, blower 56 is deactivated, and lid 30 is replaced.

Assembly 10 is designed to be portable and can be mounted to an existing fixture such as a table 40. If such an assembly is used, vacuum head 52 is designed to allow hose 50 to drop parallel to the height of table 40.

When mixing paints and solvents, or when painting, the artist should additionally use assembly 100 to aid in respiration. Assembly 100 includes mask 112. In the preferred embodiment, mask 112 is an ordinary oxygen mask with a rebreather bag 122. In operation, mask 112 is placed around the face of the artist, and adjustment of the mask to desired size is accomplished by using elastic head band 120. Mask 112 further includes nose adjustment strip 114 so that the mask may be adjusted to the artist's comfort. Further, mask 112 includes vent holes 116. In the preferred embodiment of the invention, holes 116 are covered by tape 118 so that harmful vapors cannot enter into mask. Further, this limits toxic vapor exposure through the eyes. Mask 112 is further designed so that in use, the upper surface 113 may be adjusted to create fresh air flow from below the artist's eyes to provide an exit port.

To provide clean air to mask 112, an air source, such as small air compressor (air pump) 130, is connected to mask 112. In the preferred embodiment, a compressor with a volume of 1.25 standard cubic feet per minute by using a 1/12th horsepower motor is recommended. For an individual requiring a lesser amount of air, for example, an individual performing sedentary work, smaller compressors, such as those delivering 12 liters per minute of air may be used within the scope of this invention. Although larger compressors may be used, if small capacity compressors are used together with an oxygen mask, a suitable flow of fresh air is typically provided to the artist. The compressor is designed to be mounted in fresh air outside from the work area. Preferably, the location is either elevated on a desk or shelf in a different room or most preferably, outside of a window in fresh air. Hose 128 is connected to compressor 130. Hose 128 is preferably 15 to 20 feet long and is made of surgical quality rubber tubing. The dimensions of the tubing are ⅜ inch inner diameter by ½ inch outer diameter. Longer or shorter lengths of hose 128 may be used depending on the location of compressor 130.

Air from compressor 130 passes through hose 128 into filter 126. Any suitable air filter may be used, and in the preferred embodiment, a disposable DX grade depth type coalescing air filter which is rated at a gas efficiency of 93% at 0.1 microns (droplets and/or particulate contaminants) is preferred.

After passing through filter 126, the purified air goes to line 124. Line 124 attached to mask 112 is preferably made of clear plastic, and is one quarter inch in diameter and preferably is six feet long. The end of line 124 is connected to filter 126 at coupling 123. The other end of line 124 is connected to mask 112. Thus, fresh filtered air starting from compressor 130 is supplied to mask 112.

Rebreather bag 122 on mask 112 is used to store additional oxygen. The principle unique to this respirator is that the human only uses ¼ of the oxygen available for each breath. Using a rebreather bag makes possible the use of a much smaller pump, saving on electricity rewiring costs, and thereby providing a smaller, portable, lighter product at a fraction of the cost. In addition, such an assembly is safer because there is a less likely risk of electrical overload and fire. By using compressor 130, and rebreather bag 122, a suitable flow of fresh air is provided to the artist. In the preferred embodiment, by using a 1/12th horsepower compressor and a rebreather bag, a comfortable flow of clean air using 1.25 standard cubic feet per minute is obtained. This amount is typically adequate for most artists but air requirements differ from person to person. Thus, larger compressors may be used if more air is needed. Further, depending on the activity of the artist, the quality of air breathed may be improved from at least to 80 to 100%.

It is the intent of this invention that an artist using paints containing solvents use both the palette assembly and respiration unit simultaneously. However, if one wishes, the units can be separately used as aids in ventilation.

From the above, it should be apparent that many modifications and variations of the present invention are possible. It is therefore to be understood that, within the scope of the appended claims, the invention may be practiced otherwise than as specifically described.

What is claimed is:

1. A paint ventilation enclosure for an artist when working with paints and solvents, said paint ventilation enclosure comprising:

a transparent housing having a base and sidewalls, said housing being transparent to aid in viewing paint located in said housing through said sidewalls, said housing being normally open at its top to communicate freely with the atmosphere and to gain access to paints located in said housing, a transparent palette located in said housing for holding paints, said palette being continuously flat between said sidewalls of said housing, means for supporting said palette above said base of said housing and below the top of said housing, peripheral edges of said palette being spaced inwardly from said sidewalls of said housing to allow free passage of air from above said palette to below said palette in a space defined between said peripheral edges and said sidewalls, vent means located in a sidewall of said housing above said base and below said palette for drawing vapors and fresh atmosphere downwardly from above said palette and evacuating the vapors and atmosphere out of said housing, and lid means removably mounted on top of said housing for allowing free communication of atmosphere with the interior of said housing when access to the interior of said housing is required in a first position of said lid and for sealing the interior of said housing when said lid is in a second position to prevent escape of vapors from said housing.

2. A paint ventilation enclosure as in claim 1, wherein said palette is located closer to said base than to the top of said housing.

3. A paint ventilation kit for an artist, said paint ventilation kit comprising:

a respiration unit including an air source for supplying a source of clean air, a facial mask for receiving said clean air from said air source, and connection means for connecting said air source to said mask, a housing having a base and sidewalls, said housing being normally open at its top to communicate freely with the atmosphere and to gain access to paints located in said housing;

a palette located in said housing for holding paints, means for supporting said palette above said base of said housing, side edges of said palette being spaced inwardly from said sidewalls of said housing to allow free passage of air from above said palette to below said palette, vent means located in a sidewall of said housing above said base and below said palette for drawing vapors and fresh atmosphere from above said palette and evacuating the vapors and atmosphere out of said housing, and means removably mounted on top of said housing for allowing free communication of atmosphere with the interior of said housing in a first position and for sealing said housing in a second position, said respiration unit being used in combination with said housing for preventing paint vapors from being inhaled.

4. A paint ventilation enclosure as in claim 3, wherein said housing is transparent.

5. A paint ventilation enclosure as in claim 4, wherein said palette is transparent.

6. A paint ventilation enclosure as in claim 3, wherein said palette is located closer to said base than to the top of said housing.

* * * * *